United States Patent [19]

Ohlson

[11] Patent Number: 4,699,425
[45] Date of Patent: Oct. 13, 1987

[54] CHAIR FOR USE WHEN TAKING X-RAY PICTURES

[75] Inventor: Carl-Eric Ohlson, Solna, Sweden

[73] Assignee: AO Medical Products AB, Stockholm, Sweden

[21] Appl. No.: 795,352

[22] PCT Filed: Feb. 19, 1985

[86] PCT No.: PCT/SE85/00084
§ 371 Date: Oct. 18, 1985
§ 102(e) Date: Oct. 18, 1985

[87] PCT Pub. No.: WO85/03633
PCT Pub. Date: Aug. 29, 1985

[30] Foreign Application Priority Data
Feb. 20, 1984 [SE] Sweden ............................. 8400918

[51] Int. Cl.[4] .............................................. A47C 1/02
[52] U.S. Cl. .................................... 297/349; 297/241; 297/383; 297/DIG. 4
[58] Field of Search ............... 297/349, 383, 311, 241, 297/DIG. 4; 378/177, 178, 205; 248/424, 429; 5/81 B

[56] References Cited

U.S. PATENT DOCUMENTS

| | | | |
|---|---|---|---|
| 1,977,550 | 10/1934 | Gibb | 297/327 |
| 2,293,324 | 8/1942 | Vladeff | 378/205 |
| 2,613,726 | 10/1952 | Paatero | 297/349 |
| 3,075,810 | 1/1963 | Kitsopoulos | 297/270 |
| 3,113,804 | 12/1963 | Ritter | 297/349 X |
| 3,151,910 | 10/1964 | Larson | 297/349 |
| 3,368,845 | 2/1968 | Watanabe | 297/330 |
| 4,482,184 | 11/1984 | Mincey | 297/349 |
| 4,542,915 | 9/1985 | Wheeler et al. | 297/DIG. 4 |
| 4,600,239 | 7/1986 | Gerstein | 5/81 B |

FOREIGN PATENT DOCUMENTS

| | | |
|---|---|---|
| 0011407 | 5/1980 | European Pat. Off. . |
| 2406435 | 5/1979 | France . |
| 204191 | 5/1966 | Sweden . |

Primary Examiner—James T. McCall
Attorney, Agent, or Firm—Fleit, Jacobson, Cohn & Price

[57] ABSTRACT

A chair assembly intended for use when taking X-ray pictures includes a chair and wheels for rotating and moving the chair relative to a carriage structure in the directions of the X- and Y-coordinates. Movement in the direction of these coordinates is effected by two guide frames provided with guides. A separate support frame provided with castors is arranged on the seat parts of the chair to prevent the chair from toppling or tipping. The castors of the support frame are normally located at a small distance from the underlying support surface, so as not to impede rotational and coordinate movements of respective chair members. Chair movements are controlled by a stirrup-like control bar having provided in the central portion thereof other control parts for activating the release of locking parts which lock the chair components against rotary movement and movement in the direction of the coordinates.

7 Claims, 5 Drawing Figures

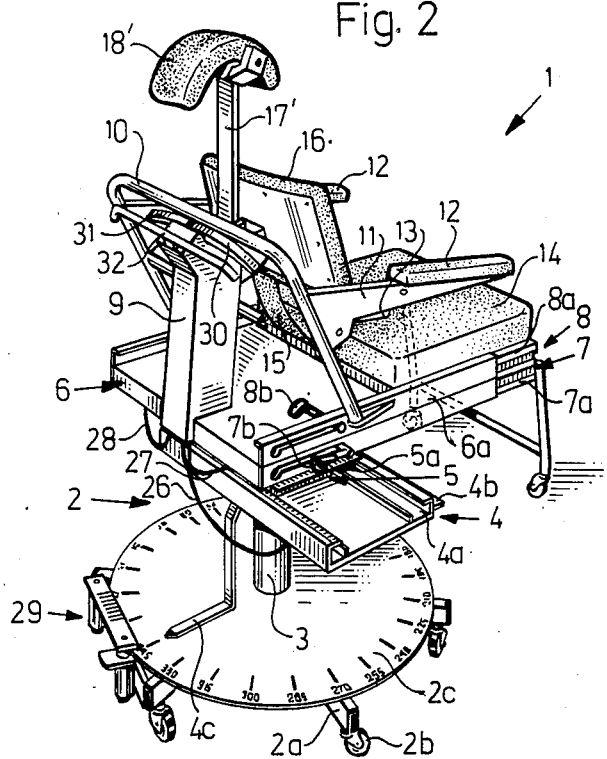
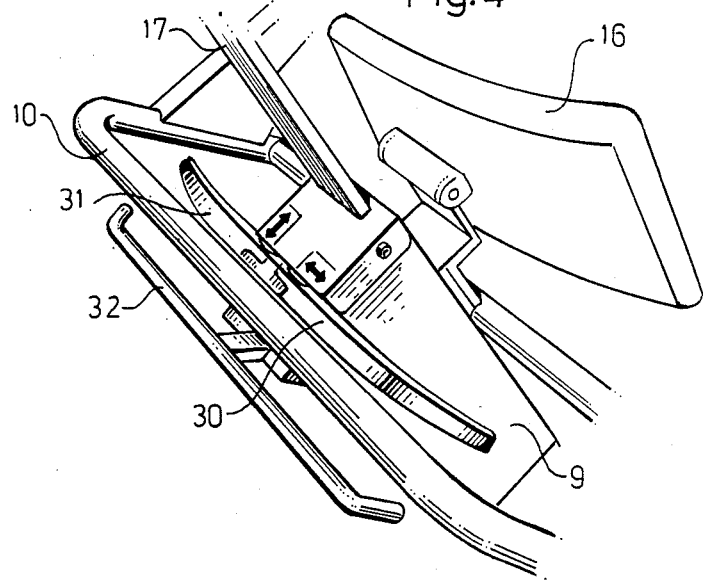

CHAIR FOR USE WHEN TAKING X-RAY PICTURES

TECHNICAL FIELD

The present invention relates to a chair assembly for use when taking X-ray pictures comprising a carriage structure fitted with swivel wheels or rollers; a chair mounted on the carriage structure and including first and second guide frames provided with guide means intended for guiding in the horizontal plane the movement of seat components in the direction of X- and Y-coordinates; bearing means for twisting or rotating the guide arms, and therewith said seat components, relative to the carriage structure; locking means for releasably locking the guide frames and the seat members against movement; control means for controlling movement of the chair on the carriage structure and for guiding rotational and coordinate movement of the guide frames; and control means for controlling the locking means for locking and releasing rotational and coordinate movement of the guide frames.

A chair of this kind can be moved, either when occupied by a patient to be X-rayed or when empty, by displacing the chair on the wheeled carriage structure and then setting it in precisely the position desired, by releasing the requisite guide frame locking means and rotating the guide frames and/or moving them in the direction of the X- and Y-coordinates.

Departing from a reference position, the position of the chair can be finely adjusted with the aid of rotational and coordinate scales located on the chair assembly.

A chair of this kind is thus an important piece of equipment when taking X-ray pictures, primarily because it contributes effectively in enabling the X-ray pictures desired to be taken correctly the first time, thereby obviating the need of re-takes and preventing the patient from being exposed to otherwise unnecessary harmful radiation resulting from the re-takes.

BACKGROUND ART

Earlier known chair assemblies of this kind are, inter alia, difficult to handle and manipulate, due partly to the unsatisfactory design and positioning of the control means for controlling chair movement and release of the locking means, and partly to the fact that, in order to ensure that the chair will not topple, the carriage structure is of such wide dimensions that it obstructs the personnel in their efforts to move and adjust the position of the chair.

The carriage structure must be given wide dimensions, because if not there is an acute risk that the seat will topple or tip when seating a patient thereon. It is often necessary to seat severely injured patients or handicapped people in the chair. These patients are often taken from a bed, wheelchair or like device and placed initially on the edge of the chair seat, whereupon the chair would immediately tip forwards if the carriage structure were not dimensioned to prevent this from happening.

The risk of the chair tipping backwards is also to be found when adjusting the setting of the chair relative to the carriage structure in order to take certain kinds of X-ray pictures.

A chair assembly for use when taking X-ray pictures and comprising a carriage structure which is overdimensioned in relation to the chair seat and which impedes the X-ray personnel in their work is found described and illustrated in EPC-A1-0 001 407 (Pfizer Inc.).

Other types of chairs intended for quite different purposes and comprising various arrangements for preventing or permitting toppling or tipping of the chair to a given extent are known to the art.

Examples of such chairs are found described and illustrated in SE-B-204 191 (Berggren), FR-B-2 406 435 (Bonneau), U.S. Pat. No. 1,977,550 (Gibb), U.S. Pat. No. 3,075,810 (Kitsopoulos), U.S. Pat. No. 3,368,845 (Watanabe).

U.S. Pat. No. 2,293,324 (Vladeff) describes a radiography process and apparatus comprising a number of hollow travelling frames which are movable relative to each other.

OBJECT OF THE INVENTION

An object of the present invention is to provide a chair of the aforementioned kind intended for use when taking X-ray pictures which is not encumbered with the disadvantages inherent with known chairs and which can be handled more readily and more easily than said known chairs and with which there is no risk of the chair tipping, despite the small dimensions of the carriage structure upon which the chair is seated.

BRIEF DISCLOSURE OF THE INVENTION

In its widest aspects, a chair according to the invention fulfilling these and other objects is characterized mainly in that the control means for controlling movement of the chair on the carriage structure and for controlling rotational and coordinate movement of the guide arms includes a control stirrup-like member mounted on the guide frame for movement in the direction of the Y-coordinate;

the control means for releasing the guide frame locking means for rotation of said guide frames and movement thereof in the direction of said coordinates is located in the vicinity of the central web-part of the stirrup-like control means; and the forward end of the seat part of the chair presents a support frame provided with pivotable wheels or rollers arranged to engage an underlying support surface, at least when a load is placed on the forward edge of the chair seat.

The design and positioning of the stirrup-like control means and the lock-release control means facilitates and simplifies handling of the chair, and the separate support frame eliminates the risk of the chair tipping, even when the dimensions of the carriage structure are small in relation to the seat. Consequently, the carriage structure need not impede the X-ray personnel when adjusting the position of the chair.

In practice, the wheels of the support frame, in the inward unloaded position of the chair seat, are located at a small distance from the underlying support surface so as not to impede the aforesaid rotational or coordinate movements.

It has been found that if the wheels of the separate support frame engage said support surface, they render it difficult to effect rotational and coordinate movement when adjusting the position of the chair. This is because the rollers of the support frame tend to move in an arcuate path in response to the wheel setting; i.e. they cannot execute the purely rectilinear movements carried out by the chair seat in the direction of the X- and Y-coordinates. On the other hand, when the rollers of the support frame are clear of the underlying support surface, they will not impede the chair-setting movements and are immediately available when required in order to avoid the risk of the chair tipping. Consequently, if possible the rollers should always be spaced a small distance from the underlying support surface, or only lightly touching the same, when carrying out the afore-said chair setting movements.

A preferred embodiment of the invention is characterized in that the control means for controlling the locking means of the guide frames is arranged on a preferably pillar-like frame member mounted on the other guide frame, said frame member also carrying a back support and accommodating a holder for a head support.

Such a preferably pillar-like frame member is useful for supporting the various control means and the back and head supports of the chair, and may also carry bowden cables or the like connecting the control means with the means for locking the control frames and rotational bearings against movement.

In practice, the stirrup-like control means preferably carries downwardly swingable arm supports. This enables an injured or handicapped person to take his/her place in the chair more easily and in certain cases one or both of the support arms may be swung down, to allow X-ray photographs to be taken of certain parts of the body more easily. The arm supports may be provided with suitably designed securing means which when subjected to pressure release a latching means so as to permit the arm supports to be dropped.

The versatility of the chair is further increased when, in accordance with a preferred embodiment, the seat part of the chair includes a lower part connected to the carriage structure and an upper seat-supporting part, said two seat parts, each activated by a respective control handle, being accommodated in the guide means of the other guide frame for movement relative to one another.

This arrangement enables the chair to be extended in the direction of the Y-coordinate, which can be to advantage in certain cases, for example when the X-ray photograph is expected to provide the best result when the patient occupies a substantially lying position in the chair.

In this respect, an advantage is gained when the back support and the seat part of the chair are joined together by means of a connecting member, this member holding the seat part in position and also being able to assist in supporting the patient when leaning in the chair or when lying substantially horizontal thereon.

In order to determine the rotational position of the chair, the carriage structure is suitably provided with a graduated scale. In this case, the first guide frame is suitably connected to an indicator which registers the angular position of the chair on the scale.

The two guide frames are also conveniently provided with suitable length scales, for determining the position of the chair in the direction of the X- and Y-cooordinates.

The carriage structure may also be provided with a foot activated securing means for releasably securing the carriage structure relative to the floor or like support surface. The provision of such means affords the advantage that the carriage structure is thereby prevented from being moved out of a set position when moving the two guide frames in the direction of the coordinates to adjust the position of the seat part of the chair.

The seat may also be designed to be swung upwardly to one or more alternative height positions in relation to the other guide frame. For example, a higher seat level may be chosen when a child is to be X-rayed. Such selective positioning of the seat in the vertical direction can be suitably effected with the aid of a simple link arrangement.

Various types of head supports may be used, depending on the type of photographic operation to be carried out. The various head supports are suitably provided with holder means of standard design arranged to fit into the pillar-like frame part, in which the said head supports can be releasably secured in different positions.

The guide frame locking means may comprise relatively simple devices, similar to disc brakes. In this respect, a spring biased brake shoe engages a disc or plate extending along one long side of the guide frames. When activating corresponding control means, the braking action is released with the aid of a Bowden-cable. When the control means is again released, the brake shoe is automatically urged against the disc or plate, to lock the guide frame.

A corresponding arrangement, although provided with a circular disc, is used to lock the chair assembly against rotation.

BRIEF DESCRIPTION OF THE DRAWINGS

A preferred embodiment of the invention will now be described in more detail with reference to the accompanying drawings.

FIG. 2 is a perspective view of the chair illustrated in FIG. 1, seen obliquely from the back in a position in which the seat part of the chair has been displaced relative to the position shown in FIG. 1, the chair assembly in this figure being provided with another type of head support.

FIG. 4 is a perspective view of a pillar-like frame member forming part of the chair assembly and carrying control means for releasing and locking movement of the guide frames.

DESCRIPTION OF A PREFERRED EMBODIMENT

Figure 1:
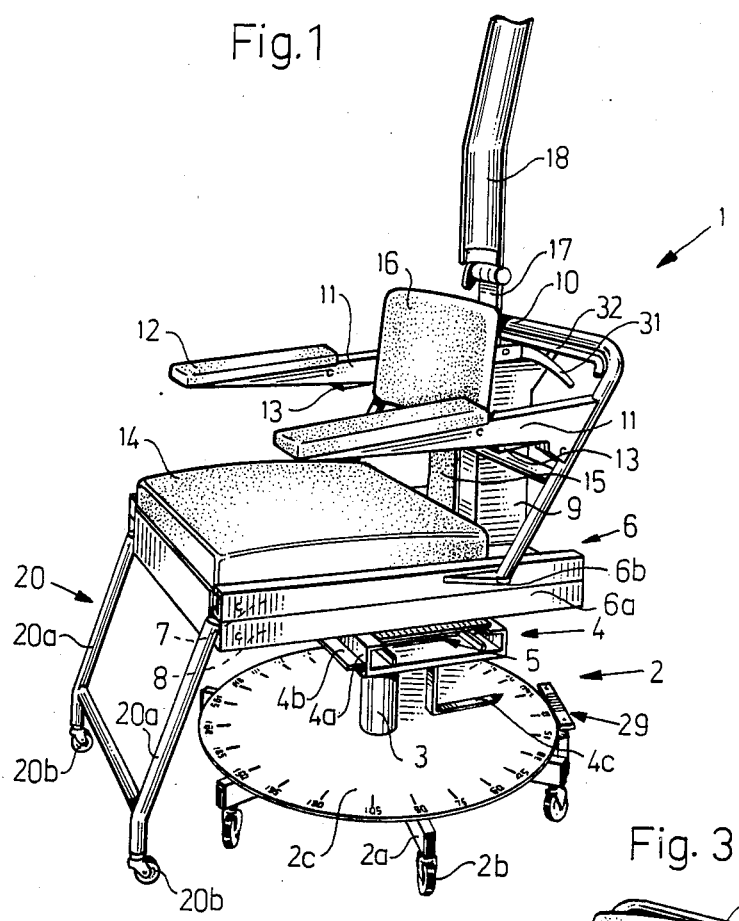
FIG. 1 is a perspective view of a chair assembly according to the invention, seen obliquely from the front.

With reference to FIGS. 1 and 2, the reference numeral 1 identifies a chair assembly intended for use when taking X-ray photographs. The chair assembly comprises a carriage structure 2 comprising a plurality of substantially horizontally extending legs 2a extending spokewise from a central hub member (not shown). Each of the legs 2a has a swivel castor 2b mounted on its free end. The carriage structure has a graduated scale 2c arranged thereon.

The dimensions of the carriage structure are small in relation to the seat part of the chair assembly, and hence the carriage structure will not present any appreciable obstacle to personnel working in the vicinity of the chair.

Extending upwardly from the carriage structure is a central pillar 3 having mounted on its upper end a bearing (not shown) for rotational movement of a first guide frame 4 said first guide frame having guide means 4a extending along the sides thereof. The guide frame 4 can thus be rotated in relation to the carriage structure. The position to which the guide frame is rotated can be read-off on the scale 2c, with the aid of an L-shaped indicator 4c.

A guide block 5 associated with an overlying second guide frame 6 is arranged in the first guide frame 4. In this way, the overlying second guide frame is accurately guided for movement in the direction of the X-coordinates relative to the first guide frame.

The upper, second guide frame 6 is also guided for movement in the direction of the Y-coordinate relative to the lower guide frame 4 in a similar manner.

The second guide frame 6 is provided with guide means 6a which displaceably accommodate a seat part comprising two mutually movable parts 7, 8 having guide strips 7a, 8a, accommodated in the guide means 6a.

Arranged at the front end of the seat part is a support frame 20 provided with swivel castors 20b which are normally located at a small distance from the floor or like underlying support surface. When the castors 20b rest against the floor, they will impede the movements made to adjust the setting of the chair. The support frame 20, comprising legs 20a and castors 20b, eliminates the risk of the chair tipping. For example, should a person be placed on the edge of the seat, the castors 20b will be urged onto the floor or like support surface and support the chair thereagainst.

The upper guide frame 6 has mounted thereon lugs 6b to which there is attached a stirrup-like control means 10. The chair can be moved on the carriage structure 2 by gripping the central part of the stirrup-like control means 10, and the two guide frames 4 and 6 can be moved in the direction of the aforesaid coordinates subsequent to releasing corresponding locking means.

As can best be seen from FIG. 2, there is provided for this purpose a control or operating means 30 affording movement in the direction of the X-coordinate, control or operating means 31 affording movement in the direction of the Y-coordinate, and control or operating means 32 affording rotary movement in the immediate vicinity of the central part of the stirrup-like control means 10. Thus, when the central part of the stirrup-like control means is gripped with both hands, all of the control means 30, 31 and 32 can be readily reached.

The aforesaid control means 30, 31 and 32 are carried on a pillar-like frame member 9, which also carries a back support 16 and presents a recess for a holder 17 and 17' respectively for a head support. As will be seen from FIGS. 1 and 2, the head rest may take different forms, the head rest of the FIG. 1 embodiment being referenced 18 and that of the FIG. 2 embodiment being referenced 18'. Other types of head rests are also conceivable.

Figure 3:
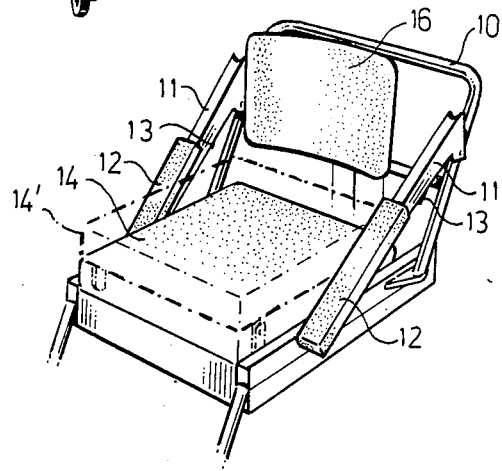
FIG. 3 is a perspective view of the seat part of the chair assembly with the arm supports in their dropped positions.

The stirrup-like control means 10 carries thereon arm supports 11 provided with support plates or pads 12. As shown in FIG. 3, the arm supports 11 can be swung downwardly, by activating a release means 13.

The seat of the chair assembly is referenced 14 and is connected to the back support 16 by means of a connecting member 15.

As indicated in FIG. 4, the seat, for example when photographing children, can be swung to a higher level, with the aid of a link mechanism, not shown.

The two seat parts 7 and 8 are movable relative to one another and can be displaced upon activation of operating arms 7b and 8b respectively arranged in slots in the one guide means 6a of the upper guide frame 6.

The movement of the guide frames and seat parts respectively in the direction of the coordinates is effected with the aid of ball bearings.

Figure 5:
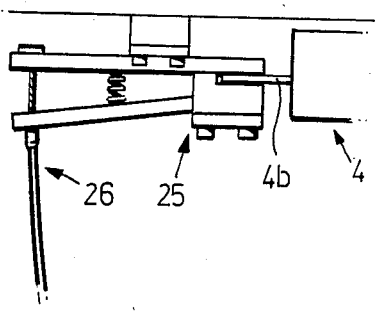
FIG. 5, finally, is a front view of a disc-brake type locking arrangement for one of the guide frames.

The control means 30, 31 and 32 activate, via Bowden-cables 26, 27 and 28 respectively, a locking mechanism comprising a brake shoe 25 (FIG. 5) arranged to bear against a plate. FIG. 5 illustrates the first guide frame 4 having arranged on the outside thereof a brake disc 4b against which the brake shoe 25 engages. When activating the control or operating means 30, the brake shoe 25 is moved away from the plate 4b, so as to enable movement in the direction of the X-coordinate. When the desired position has been reached, the control means 30 is released, causing the brake shoe 25 to be moved immediately to its locking position.

Other movements are locked and released in a corresponding manner.

Activation of the seat part 7 by means of the operating handle 7b for forward movement of the seat 14 also results in forward movement of the carriage structure 20, in the manner illustrated in FIG. 2.

I claim:

1. A chair assembly for use when taking X-ray pictures comprising:
    a carriage structure fitted with wheels or castors first means for rolling said carriage structure to a desired location;
    a chair having seat parts, said chair being mounted on the carriage structure and including first and second guide frames provided with guide means for guiding in the horizontal plane the movement of said seat parts in the direction of X- and Y-coordinates;
    bearing means for rotation of said guide frames and therewith also said seat parts, relative to the carriage structure;
    locking means for releasably locking said guide frames and said seat parts against movement;
    first control means for controlling movement of said chair relative to said carriage structure and for guiding rotational and coordinate movement of said guide frame;
    second control means for activating said locking means to lock and release rotational and coordinate movement of said guide frames, said first control means including a stirrup-like control member mounted on one of said guide frames for movement of said frame in the direction of the Y-coordinate;
    said second control means being arranged adjacent to a central part of said stirrup-like control member; and
    an outermost part of said chair being formed by said seat parts, said seat parts having arranged on their forwardmost ends a support frame provided with second means for rolling and engaging the underlying support surface as a result of a load being placed on the forwardmost ends of said seat parts.

2. A chair assembly according to claim 1, wherein said second means, at least in the unloaded position of said seat parts are located at a small distance from the underlying support surface, so as to avoid impeding rotational or coordinate movements of respective chair components.

3. A chair assembly according to claim 1, wherein said second control means for activating the guide frame locking means are arranged on a pillar-like frame member mounted on said one guide frame, said frame member also having arranged thereon a back support and a holder for a head support.

4. A chair assembly according to claim 1, wherein said stirrup-like control member carries downwardly swingable arm supports of said chair.

5. A chair assembly according to claim 1, wherein said seat parts comprise a lower part connected to said support frame and an upper part carrying a seat, each of said seat parts being guided for relative movement in guide means arranged in said one guide frame and being activated by a control handle.

6. A chair assembly according to claim 1, wherein said carriage structure has provided thereon a graduated scale for indication of the rotational position of the seat of said chair.

7. A chair assembly according to claim 6, wherein said guide frames are provided with length scales for determining the position of respective chair components in the directions of the X- and Y-coordinates.

* * * * *